US012714362B2

(12) United States Patent
Howard

(10) Patent No.: US 12,714,362 B2
(45) Date of Patent: Aug. 25, 2026

(54) FUNDAMENTAL CODE UNIT OF THE BRAIN: TOWARDS A NEW MODEL FOR COGNITIVE GEOMETRY

(71) Applicant: Genesis Intelligence, LLC, Jacksonville, FL (US)

(72) Inventor: Newton Howard, Potomac, MD (US)

(73) Assignee: Genesis Intelligence, LLC, Jacksonville, FL (US)

(*) Notice: Subject to any disclaimer, the term of this patent is extended or adjusted under 35 U.S.C. 154(b) by 293 days.

(21) Appl. No.: 18/432,595

(22) Filed: Feb. 5, 2024

(65) Prior Publication Data

US 2024/0172992 A1 May 30, 2024

Related U.S. Application Data

(63) Continuation of application No. 16/841,513, filed on Apr. 6, 2020, now Pat. No. 11,890,108, which is a (Continued)

(51) Int. Cl.

*A61B 5/00* (2006.01)
*A61B 5/055* (2006.01)

(Continued)

(52) U.S. Cl.

CPC ............ *A61B 5/4839* (2013.01); *A61B 5/055* (2013.01); *A61B 5/112* (2013.01); *A61B 5/24* (2021.01); *A61B 5/245* (2021.01); *A61B 5/30* (2021.01); *A61B 5/369* (2021.01); *A61B 5/407* (2013.01); *A61B 5/4082* (2013.01); *A61B 5/4088* (2013.01); *A61B 5/4803* (2013.01); *A61B 5/4824* (2013.01); *A61B 5/7282* (2013.01); *A61M 21/02* (2013.01); *A61N 1/00* (2013.01);

(Continued)

(58) Field of Classification Search

CPC .................................................. A61B 5/4839
USPC ........................................................ 600/544
See application file for complete search history.

(56) References Cited

U.S. PATENT DOCUMENTS

| | | | | |
|---|---|---|---|---|
| 2003/0040080 A1* | 2/2003 | Miesenbock | .... | C07K 14/43581 514/703 |
| 2004/0019370 A1* | 1/2004 | Gliner | ................ | A61N 1/36017 607/48 |
| 2007/0225674 A1* | 9/2007 | Molnar | ............. | A61N 1/36067 607/116 |

FOREIGN PATENT DOCUMENTS

| | | | | |
|---|---|---|---|---|
| WO | WO-2008066731 A2 * | 6/2008 | ............ | G06N 3/065 |

* cited by examiner

*Primary Examiner* — Nicole F Johnson
(74) *Attorney, Agent, or Firm* — Neo IP

(57) ABSTRACT

In embodiments, devices, methods and systems to analyze the different mediums of brain function in a mathematically uniform manner may be provided. For example, in an embodiment, a computer-implemented method for determining structure of living neural tissue may comprise receiving at least one signal from at least one read modality, the signal representing at least one physical condition of the living neural tissue, determining action potentials based on the signals received from the read modalities, determining frequency oscillations based on the signals received from the read modalities and the action potentials, determining neuron network structures based on the photonic signals received from the read modalities, the action potentials, and the frequency oscillations, wherein the neuron network structures are determined using a Maximum Entropy model, and mapping brain region activation by S+/R− events to observable linguistic events using the Maximum Entropy model.

15 Claims, 6 Drawing Sheets

Related U.S. Application Data continuation of application No. 16/000,783, filed on Jun. 5, 2018, now Pat. No. 10,624,578, which is a continuation-in-part of application No. 15/988,292, filed on May 24, 2018, now Pat. No. 10,617,348, which is a continuation-in-part of application No. 15/219,255, filed on Jul. 25, 2016, now Pat. No. 10,154,812, which is a continuation of application No. 13/747,448, filed on Jan. 22, 2013, now Pat. No. 9,399,144, which is a continuation-in-part of application No. 13/083,352, filed on Apr. 8, 2011, now abandoned, which is a continuation-in-part of application No. 12/880,042, filed on Sep. 10, 2010, now abandoned.

(60) Provisional application No. 62/515,133, filed on Jun. 5, 2017, provisional application No. 62/510,519, filed on May 24, 2017, provisional application No. 61/588,666, filed on Jan. 20, 2012, provisional application No. 61/322,158, filed on Apr. 8, 2010, provisional application No. 61/241,314, filed on Sep. 10, 2009.

(51) Int. Cl.

| | |
|---|---|
| ***A61B 5/11*** | (2006.01) |
| ***A61B 5/24*** | (2021.01) |
| ***A61B 5/245*** | (2021.01) |
| ***A61B 5/30*** | (2021.01) |
| ***A61B 5/369*** | (2021.01) |
| ***A61M 21/02*** | (2006.01) |
| ***A61N 1/00*** | (2006.01) |
| ***A61N 2/00*** | (2006.01) |
| ***A61N 5/06*** | (2006.01) |
| ***A61N 7/00*** | (2006.01) |
| *A61M 21/00* | (2006.01) |
| *A61N 1/36* | (2006.01) |
| *A61N 5/10* | (2006.01) |

(52) U.S. Cl.

CPC ........... *A61N 2/006* (2013.01); *A61N 5/0618* (2013.01); *A61N 5/0622* (2013.01); *A61N 7/00* (2013.01); *A61B 5/4076* (2013.01); *A61B 2576/026* (2013.01); *A61M 2021/0027* (2013.01); *A61M 2021/0044* (2013.01); *A61N 1/36014* (2013.01); *A61N 1/36071* (2013.01); *A61N 2005/0661* (2013.01); *A61N 2005/1087* (2013.01); *A61N 2007/0026* (2013.01); *A61N 2007/0073* (2013.01); *A61N 2007/0082* (2013.01)

Fig. 2

| Symbol | Description |
|---|---|
| $S$ | *Brain regions* |
| $A$ | *Activation sets* |
| $A$ | *Concept activation sets* |
| $W$ | *Concepts* |
| $P$ | *Concept activation mapping* |
| $\Xi$ | *Axiology* |
| $F$ | *Parity mapping* |
| $\mu$ | *Weight mapping* |

FUNDAMENTAL CODE UNIT OF THE BRAIN: TOWARDS A NEW MODEL FOR COGNITIVE GEOMETRY

CROSS-REFERENCE TO RELATED APPLICATIONS

This application is a continuation of U.S. patent application Ser. No. 16/841,513, filed Apr. 6, 2020, now U.S. Pat. No. 11,890,108, issued Feb. 6, 2024, which is a continuation of U.S. patent application Ser. No. 16/000,783, filed Jun. 5, 2018, now U.S. Pat. No. 10,624,578, issued Apr. 21, 2020 which is a continuation-in-part of U.S. patent application Ser. No. 15/988,292, filed May 24, 2018, now U.S. Pat. No. 10,617,348, issued Apr. 14, 2020, which claims the benefit of U.S. Provisional Application No. 62/510,519, filed May 24, 2017, and which is a continuation-in-part of U.S. patent application Ser. No. 15/219,255, filed Jul. 25, 2016, now U.S. Pat. No. 10,154,812, issued Dec. 18, 2018, which is a continuation of U.S. patent application Ser. No. 13/747,448, filed Jan. 22, 2013, now U.S. Pat. No. 9,399,144, issued Jul. 26, 2016, which claims the benefit of U.S. Provisional Application No. 61/588,666, filed Jan. 20, 2012, and which is a continuation-in-part of U.S. patent application Ser. No. 13/083,352, filed Apr. 8, 2011, now abandoned, which is a continuation-in-part of U.S. patent application Ser. No. 12/880,042, now abandoned, filed Sep. 10, 2010, which claims the benefit of U.S. Provisional Application No. 61/322,158, filed Apr. 8, 2010, and U.S. Provisional Application No. 61/241,314, filed Sep. 10, 2009, which are incorporated by reference herein in their entirety. This application further claims the benefit of U.S. Provisional Application No. 62/515,133, filed Jun. 5, 2017, which is incorporated by reference herein in its entirety.

BACKGROUND

The present systems and methods relate to devices, methods and systems for analyzing the different mediums of brain function in a mathematically uniform manner.

As humans living in a complex world, our success and survival depend on our ability to simplify and understand what we observe of our environment, a process of formulating and reformulating received information into cognitive models and systems. Cognitive agents organize objects, concepts, and themselves into schemes consisting of fundamental units, which then constitute an overarching structure. Once created, cognitive agents continue to develop and refer to these models with every new experience and observation, in fact, these models could be said to form the basis of all our subsequent cognitive processes. For researchers and theorists working to understand human brain function, the significance of these behaviors supports the effort to identify a "fundamental unit" of thought. By defining and then organizing these units into the larger processes that form human consciousness, we might advance new ways of thinking about cognition and awareness.

Existing research has gravitated towards the quantum and electromagnetic explanations of consciousness due to the fact that so little is known about this phenomenon. However, because cognition itself is not simply a single natural process but a group of processes that we categorize as composing conscious thought, any attempt to model these processes must take multiple interdependent levels of analysis into account. This approach has led to a fundamental rift between several disciplines that each contribute directly to our understanding of the brain, such as philosophical, psychological and neuroscientific perspectives.

A comprehensive understanding of cognition presupposes more than simply a grasp of the physical and chemical processes at work. The highest, or philosophical, level of analysis serves as an ideal starting point because in order to model cognition, there needs to exist some consensus as to what it is, or at least some criteria that a model must satisfy. Philosophical models such as the duality of mind and brain must frame the discourse on cognition, because intelligent thought does not occur in a vacuum; it needs to be defined in both relative and absolute terms. In addition, to conflate the processes that comprise intelligent thought with the perception of those processes by other intelligent thinkers would not lead to an applicable model. In order to usefully quantify the physical processes comprising cognition, devices, methods and systems to analyze the different mediums of brain function in a mathematically uniform manner are needed.

The brain contains approximately 100 billion neurons, each of which has roughly the processing capability of a small computer. A considerable fraction of the 100 billion neurons are active simultaneously and do much of their information processing through interactions with one another. Frequency oscillations in neuronal and electronic-related releases are the underlying causes of most brain disorders. As such, it is crucial to understand the nature of such frequencies, their causes, their ranges, and the relation of each range to each disorder. In addition, this understanding will reinforce the psychological analysis as well.

Accordingly, a need arises for devices, methods and systems to analyze the different mediums of brain function in a mathematically uniform manner.

SUMMARY

In embodiments, devices, methods and systems to analyze the different mediums of brain function in a mathematically uniform manner may be provided. These devices, methods and systems may manifest at several levels and ways relating to brain physiology, including neuronal activity, molecular chirality and frequency oscillations. To best understand the unitary system, it is necessary to comprehend its expression through each of these mediums instead of focusing on any single level.

For example, in an embodiment, a computer-implemented method for determining structure of living neural tissue may comprise receiving at least one signal from at least one read modality, the signal representing at least one physical condition of the living neural tissue, determining action potentials based on the signals received from the read modalities, determining frequency oscillations based on the signals received from the read modalities and the action potentials, determining neuron network structures based on the photonic signals received from the read modalities, the action potentials, and the frequency oscillations, wherein the neuron network structures are determined using a Maximum Entropy model, and mapping brain region activation by S+/R− events to observable linguistic events using the Maximum Entropy model.

In embodiments, the neuron network structures may be determined using a Maximum Entropy model. The method may further comprise determining axiological structures based on the signals received from the read modalities, the action potentials, the frequency oscillations, and the determined neuron network structures. The axiological structures may be determined using a Unitary System in which preconceptual image schemata include axiological parameters with bipolar properties having positive and negative associations. The method may further comprise determining linguistic structures based on the signals received from the read modalities, the action potentials, the frequency oscillations, the determined neuron network structures, and the determined axiological structures. The linguistic structures may be determined by assessing linguistic symbolic units on an axiological scale.

In an embodiment, a system for determining structure of living neural tissue may comprise a processor, memory accessible by the processor, and computer program instructions stored in the memory and executable by the processor to perform receiving at least one signal from at least one read modality, the signal representing at least one physical condition of the living neural tissue, determining action potentials based on the signals received from the read modalities, determining frequency oscillations based on the signals received from the read modalities and the action potentials, determining neuron network structures based on the photonic signals received from the read modalities, the action potentials, and the frequency oscillations, wherein the neuron network structures are determined using a Maximum Entropy model, and mapping brain region activation by S+/R− events to observable linguistic events using the Maximum Entropy model.

In an embodiment, a computer program product for determining structure of living neural tissue may comprise a non-transitory computer readable storage having program instructions embodied therewith, the program instructions executable by a computer, to cause the computer to perform a method comprising receiving at least one signal from at least one read modality, the signal representing at least one physical condition of the living neural tissue, determining action potentials based on the signals received from the read modalities, determining frequency oscillations based on the signals received from the read modalities and the action potentials, determining neuron network structures based on the photonic signals received from the read modalities, the action potentials, and the frequency oscillations, wherein the neuron network structures are determined using a Maximum Entropy model, and mapping brain region activation by S+/R− events to observable linguistic events using the Maximum Entropy model.

BRIEF DESCRIPTION OF THE DRAWINGS

The details of the present invention, both as to its structure and operation, can best be understood by referring to the accompanying drawings, in which like reference numbers and designations refer to like elements.

FIG. 2 is an exemplary illustration of symbols used in an outlined concept set framework.

DETAILED DESCRIPTION

Figure 1:
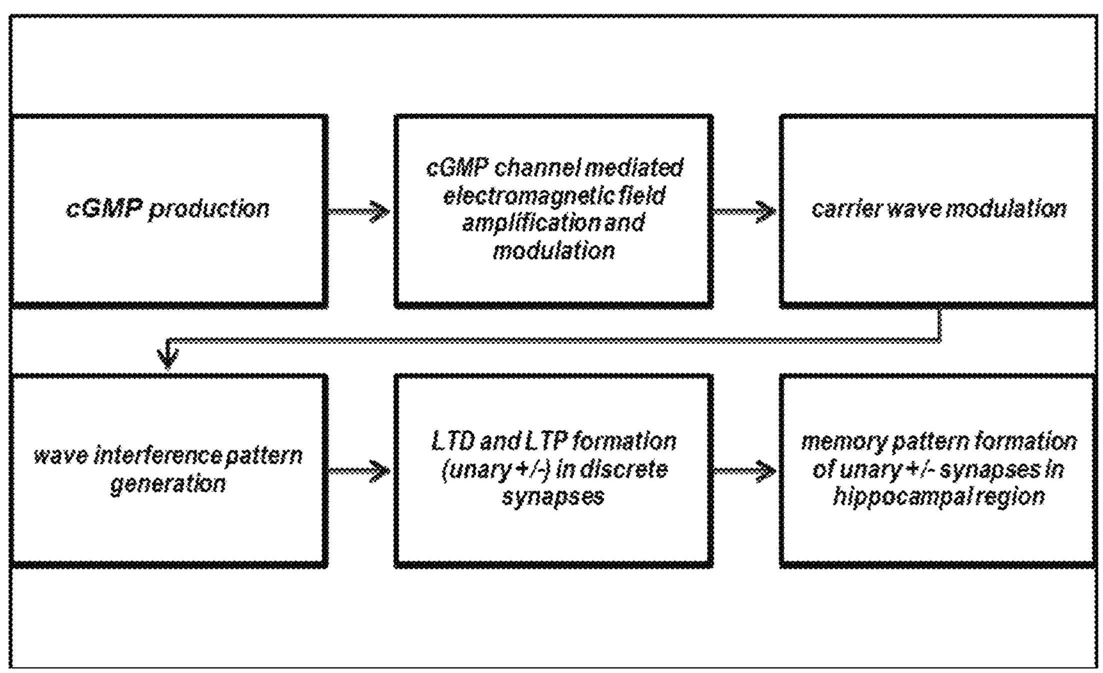
FIG. 1 is an exemplary illustration of a process-level view of Fundamental Code Unit encoding within the brain.

The present invention relates to a non-invasive system with diagnostic and treatment capacities that use a unified code that is intrinsic to physiological brain function. In an embodiment of the present invention, an approach to the treatment of disorders that supplements existing diagnostic and treatment methods with robust quantitative data analysis are presented. This is achieved by a unification of cognitive and neural phenomena known as the Fundamental Code Unit (FCU), representing identifiable patterns of brain activity at the submolecular, molecular, and cellular levels (intra-brain communications), as well as their manifestations in thought and language (inter-brain communications). The FCU is described in the following applications, which are incorporated by reference herein in their entirety: U.S. Provisional Application No. 61/241,314, filed Sep. 10, 2009, U.S. Provisional Application No. 61/322,158, filed Apr. 8, 2010, U.S. Provisional Application No. 61/588,666, filed Jan. 20, 2012, U.S. Provisional Application No. 62/510,519, filed May 24, 2017, U.S. Provisional Application No. 62/515,133, filed Jun. 5, 2017, U.S. patent application Ser. No. 12/880,042, filed Sep. 10, 2010, U.S. patent application Ser. No. 13/083,352, filed Apr. 8, 2011, U.S. patent application Ser. No. 13/747,448, filed Jan. 22, 2013, now U.S. Pat. No. 9,399,144, issued Jul. 26, 2016, U.S. patent application Ser. No. 15/219,255, filed Jul. 25, 2016, and U.S. patent application Ser. No. 15/988,292, filed May 24, 2018.

The FCU utilizes read and write modalities to affect living tissue, such as neural tissue of the brain. The above-referenced documents describe a number of such modalities that may be utilized by the FCU. Embodiments of the present systems and methods may include modalities that operate by way of Photonic Signaling, as described below.

The Fundamental Code Unit (FCU) aims to unify the molecular, cellular, neural, cognitive, and linguistic layers of neurophysiological operation and postulates that all output of the brain originates from a single unit. These fundamental units are indivisible, reconfigurable, parallel and recursive. Like the four nitrogenous bases comprising DNA, units are relatively simple when compared to the structures they create. FCU units are transformed into brain function through mechanisms powered by unitary operators "unary plus" (+) and "unary minus" (−). In this paper, we explain the FCU theory and provide a detailed example of its operation within neocortical networks. Information is transmitted by several means within the neocortex, including chemical, electrical, mechanical and optical. While each of these transmission systems run the FCU code, we will specifically discuss photonic activity within the neocortex that is transduced into synaptic membrane potential changes via a cGMP-dependent mechanism, similar to that in the retina. In parallel to this process, the G protein/cGMP phosphodiesterase pathway is catalyzed via photostimulation and regulates membrane potentials through cGMP-gated ion channels, using a system of unitary operators. These systems are mediated by neuropsin (OPN5), a bistable photopigment. Observations of photonic signaling suggest that this self-regulating cycle may regulate neuroplasticity, both during memory formation and in adaptive responses.

Introduction. Fundamental Code Unit (FCU) theory postulates that all output of the brain originates from single units. These fundamental units are reconfigurable, recursive, and indivisible. Moreover, they exist in parallel, a characteristic integral to the complexity of cognition. Like building blocks, these units combine in many different patterns to produce thought and behavior. As with DNA, fundamental code units are themselves simple when compared to the complex structures they create. We posit that units are transformed into brain computation through mechanisms powered by unitary operators—binary schematics, "unary plus' (+) and "unary minus" (−).

Information is transmitted by chemical, electrical, mechanical and, as we emphasize herein, optical means within neocortical networks. We show that each of these layers and mechanisms adheres to FCU theory. We will specifically discuss photonic activity, which is transduced into synaptic membrane potential changes via a cGMP-dependent mechanism similar to that in the retina. In parallel, the G protein/cGMP phosphodiesterase pathway is catalyzed via photostimulation and regulates membrane potential through cGMP-gated ion channels, using a system of unitary operators. Photonic control is mediated by the bistable photopigment neuropsin (OPN5) in neocortical synapses. Recently, photonic signaling has been observed which may help regulate neuroplasticity.

1. INTRODUCTION. The FCU theory may be presented in terms that are more accessible to practitioners within a broad range of current scientific endeavor, both basic and applied: neuroscience in particular, but also psychology, sociology, and electrical engineering (e.g., circuit design theory and practice). Within the framework of this new paradigm, a view of several lines of information emerging from molecular, cellular and behavioral neuroscience that are both supportive of this new paradigm and—most importantly—suggest how the FCU hypothesis can be tested, the goals being to elucidate the neural correlates of the FCU, and apply this information to new therapeutic strategies as well productively addressing the broader quasi-philosophical questions cited above.

In embodiments, a novel multi-disciplinary quantum physics approach is provided for developing a theory of concepts that solves the combination problem, i.e. to deliver a description of the combination of concepts. At this level, a better understanding of the quantum activity needed to affect human behavior in a meaningful way may be developed. Specifically, two chemical and physical mechanisms within the brain may have a direct impact on cognitive function. The first is the role of transduction-associated channels in the hippocampal region of the brain that regulate visual stimulus processing. Since these channels rely on similar mechanisms to the neural correlates of language, but are much better mapped and known, it is possible to apply what is known about them to the link between language and cognition. Second is the prominence of astrocytes containing key components of an amplification and transduction cascade (a CGMP-triggered transduction channel). These astrocytes are much larger in humans than in primates, suggesting an important neuro-cognitive link. Based on what is known about the physiology of astrocytes, they may play a key role in signal amplification and transduction, wherever they are found in the brain.

Finally, neuroplasticity-based changes that produce memories, such as long term synaptic depression (LTP) and long term synaptic facilitation (LTD), may be examined in order to determine FCU-based cognitive variance over long periods of time.

2. ANALYTICAL GOALS. An analytically rigorous, comprehensive approach to modeling human cognition has myriad applications; in addition to better understanding processes such as language acquisition and developmental neurobiology, it can aid in predictive behavioral analysis and organizational dynamics. There are two related questions. First, how much neuronal activity constitutes a coherent thought? Understanding patterns of neuronal activity is a prerequisite to determining which aspects of those patterns correspond to the phenomenon of the individual thought, aspects that we hold to constitute the FCU. Second, do some types of neuronal activity compose cognition while others do not? Since the number of neural networks in which any given neuron can exist is limited only by the connections it forms with its neighbors, it is possible that some activity contributes to conscious brain function, while some does not. Discerning the type of neuronal activity that contributes to cognition at a single-cellular level will similarly contribute to the search for a fundamental unit that can be used to classify thought.

A series of exemplary case studies, or applications of the human brain, may be helpful to demonstrate the mapping of the physical processes observed at the chemical level to cognitive changes that are exhibited through behavior, such as the development of language skills and the notion of linguistic semantic primitives. Since these concepts are the building blocks of coherent communicated thought, the interface between them and a more basic, fundamental cognitive code can shed important light on human thought processes. Ultimately, there are three broad conceptual categories: a) FCU as the unit of cognition: to devise a coherent mapping of the FCU to thought components, linguistic constructs and structures, as well as behavior; b) mind/body dualism a defining component of the conceptual framework of cognition: to develop a mathematical framework with explanatory and predictive value, even though it is not possible to directly observe or objectify the concepts explained therein; and c) to delineate precisely what can be measured within the brain and how—together with external observations of language, behavior—the nature of the FCU can be precisely quantified.

3.1 The Molecular Basis for Cognition. Amino acid molecules are constituted by amine group, a carboxylic acid group and a side-chain that varies between different amino acids. The key elements of an amino acid are carbon, hydrogen, oxygen, and nitrogen. The amino acid phenylalanine is of particular importance to the construction of neurotransmitter precursors. There are several important neurotransmitters of the chemical components of cognition. Some of these major neurotransmitter classes include: Amino acids (glutamate, aspartate, D-serine, γ-aminobutyric acid (GABA), glycine); Monoamines and other biogenic amines (dopamine (DA), norepinephrine (noradrenaline; NE, NA), epinephrine (adrenaline), histamine, serotonin (SE, 5-HT)); and Others (acetylcholine (ACh), adenosine, anandamide, nitric oxide)

Evidence based on analysis of short-term memory (SM) processes, or "working memory," shows that persistent firing of the corresponding neuronal networks is required for the encoding of information. Assuming that working memory is always active during conscious moments, this suggests that at the level of the single neuron, state changes are constantly occurring, not unlike memory cells in the random-access memory of a personal computer. However, it is unclear whether these state changes necessarily correspond to numerically-based distinctions, or whether more subtle state differences are responsible for the communication of information.

3.2 Metabolic Involvement in Conscious Thought. The link between long-term memory (LM) and cellular/synaptic processes such as long-term potentiation/depression (LTP/LTD) requires some sort of structural changes/protein synthesis: 1) Changing neurotransmitter receptor expression; 2) Increasing synapse size; and 3) Changing synapse anchoring.

ADP/ATP (Adenosine Diphosphate/Adenosine Triphosphate) represents the major energy source in neurons and glial cells, and is therefore required for long-term memory preservation. Apart from ATP/ADP fueling persistent activity by driving ATP/ADP-dependent ionic pumps and the maintenance of synaptic receptors, the study of ATP/ADP has shown it to be directly linked to the emergence of persistent activity through its modulation of ATP modulated potassium channels. ADP/ATP energy per activation for each unit of actions and columns (assuming C is a fundamental module of the perceptual system) meets the activation requirement as the force for persistent activity.

Recent near-infrared studies have shown that an increase in ATP availability leads to cognitive enhancement. for example, this purinergic signaling phenomenon shows the involvement of ATP/ADP-mediated signaling through neuronal and glial receptors in nearly every aspect of brain function. Further, this is involvement of ATP/ADP-mediated signaling through neuronal and glial receptors in many aspects of brain function.

3.3 Neurological Signaling. Evolution has provided humans with a multilayer Central Nervous System; that is, a given neuron can be involved in the transmission of vast numbers of simultaneous signals. By this process, one neuron releases a neurotransmitter into a small space (the synapse) that is adjacent to another neuron. Neurotransmitters must then be cleared from the synapse efficiently so that it can be ready to function again as soon as possible.

In neurons, information is transmitted as “spikes”; it is unclear how exactly these spikes encode information, and there is a continuing debate in the field about whether the timing of these spikes is an important informational component. What comprises these spikes is the activity of voltage-gated ion channels, which are themselves stochastic mechanisms, or nonlinear systems that have some significant degree of signal noise.

Since these spikes, or instances of stochastic resonance, are the basis for information transmission in the brain, it follows that an attempt to model cognition from the lowest level up should begin at the signal-unit level. While it is easily discerned that thoughts are necessarily composed of these spikes, and in a literal sense they form the basic units of thought, this perspective offers little new insight—there needs to be some useful, repeated composition of these spikes that is observed in cognitive process that researchers can categorize as a basic unit of thought.

Neural oscillation is an observed repetitive pattern of these energy spikes that results from the synchronization of neurons firing simultaneously. Changes in the pattern of this synchronization have been linked to perceptual and motor processes, so the underlying process that drives neurons to fire in sync merits further research as an electro-chemical mechanism for cognition. Whether it is the spike itself or the interspike interval that is most significant to the transmission of information between networks of neurons, the overall process of synchronization still has a fundamental bearing on the conscious thought process. The relatively nascent status of neurological stochastic signaling research makes experimentation on neuron spike timing difficult since statistical approaches such as principal component analysis tend not to offer insight into the actual coding strategies of neurons. This suggests that while there may be determinable correlations between neuron spikes and cognition-influenced conscious behavior, they would not be fine-grained enough to tie specific spike patterns to thought processes.

4. COGNITIVE GEOMETRY: TOWARDS A NEW APPROACH TO BRAIN DISORDERS. Existing treatments for cognitive disorders fall into two major categories: symptom management and blanket chemical treatment. In the former case, not enough is known about the disorder to stem the root cause, so secondary treatments aimed at alleviating the resulting symptoms form the bulk of treatment efforts. Blanket chemical treatment, on the other hand, involves the imprecise use of pharmaceuticals against a single diagnostic profile, but often with a host of side effects that result from the high usage of medication to achieve effectiveness against the original disorder. Both reflect a need for a deeper, more fine-grained understanding of cognitive disorders.

To that end, the problem of cognitive dysfunction may be modeled as one of protein structure pathology, or misfolding. Using computational cognitive research including the Unitary System and the accompanying Fundamental Code Unit (FCU), a new means for understanding disorders such as Bipolar Disorder (BD) and Alzheimer’s Disease (AD) may be provided. For example, BD and AD are caused by the mechanisms of neurological oscillation and protein deformities, respectively. Since a protein’s structure typically provides the basis for its function, the conformational rearrangements of proteins in response to ligand binding, mutation, and covalent modification very often underlie biologically important molecular events, whether in the normal course of transducing a signal or through deleterious misfolding. The specific functions of proteins are dictated by their shapes. Thus, biologically important molecular events often consist of a change in shape or configuration of key proteins, whether as a response to ligand binding, mutation, or covalent modification. Since each of these processes introduces the possibility of deleterious misfolding, they each merit a closer examination in terms of the scope of their potential effects. Such examination may allow derivation of the causes of diseases from a closely defined set of empirical parameters instead of searching for a fit between known symptoms and protein misfolding phenomena.

Using misfolding as a causal basis, specific changes in protein structure, ranging from allosteric motion to the onset of aggregation disease, may be predicted and explained. Ultimately, the primary research question is what causes the misfolding, but in this case it may be treated as miscoding, or a deleterious alteration in the cognitive or neurobiological effects of misfolding, instead of simply the physical phenomenon of misfolding. The question is which foldings and misfoldings serve as the correct or defective signal in the chain of Fundamental Code Unit (FCU) expressions. Then, by controlling the extant signaling mechanism through a ‘write’ method similar to the computational equivalent, changes may be seen on the macro, or folding, level. Even in the absence of abnormalities or disorders, cognition is characterized by a diversity of signals and patterns. Measurement of the ventrolateral prefrontal cortex, for instance, may show a number of significant differences in cognitive tuning functions in tasks requiring different sequencing and cognitive control demands.

4.1 Case Study. As an exemplary case study, the vestibular system is a promising perspective from which to assess brain function relative to protein folding and misfolding, since it is located primarily in the mesencephalon and receives input from proprioception receptors from throughout the body. In addition, it is integrated with input from the cerebellum, semicircular canals and visual and auditory system and relays information and coordinates the motor system to maintain balance. This serves to keep the body in a neutral position so that it is sensitive to critical environmental perturbations.

4.2 FCU and the Uncertain Structure of Cognition. An example of a process-level view of Fundamental Code Unit encoding within the brain is shown in FIG. 1.

Cognition is an inherently complex, and thus necessarily uncertain, phenomenon. Specifically, the mere occurrence of a thought or brain region activation can influence future neural manifestations of the same concept. Thus, a statistically-founded model is necessary, and the Maximum Entropy model (Maxent) may be used. Examining microscopic and molecular phenomena, along with macroscopic phenomena such as linguistics and behavioral cues, the distinctions between predictive and explanatory models may be elucidated, and the problems that occur when they are used in conjunction may be determined. Because neuromathematics (or "mathematical medicine,") is so interdisciplinary and requires such collaboration, differences in expertise and background among researchers may present a number of collaboration problems. For instance, there is no common language (yet) to discern exactly what a neuromathematical model is, in terms of its capabilities and intended applications.

One of the application of Maxent to FCU is the concept set. As described below, apart from its intuitive network configuration that resembles the structure of cognition itself, the computational power of the FCU lies in its ability to create a "database" of concept, physical processes, and linguistic linkages that tend to occur at given mind states. Populating such a database to the point that it resembles the human brain in both structural configuration and performance ability requires a method of creating connections between otherwise disparate linguistic and cognitive constructs. A Maxent-based concept for modeling language statistically may be further applied to the mapping of brain region activation by S+/R− events to observable linguistic events.

Figure 3:
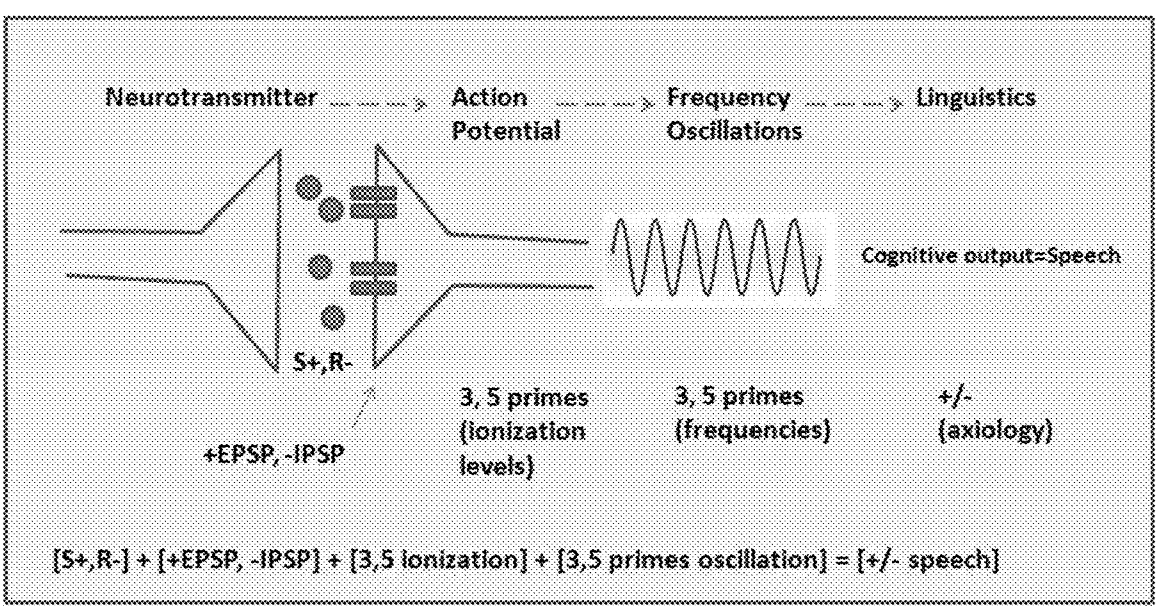
FIG. 3 is an exemplary illustration of a multi-level code translation from neuronal interaction to cognition and language.

An example of multi-level code translation from neuronal interaction to cognition and language is shown in FIG. 3. FIG. 3 illustrates the translation of neural code, from neurotransmitter and spike/pulse sequences, to action potentials, to frequency oscillations, and finally to cognitive output including speech and behavior. Original neural encoded information might be meaningful; however, the meaning is not dependent on the interpretation. In neurological disorders, post-synaptic neurons may not be able to interpret and act on meaningful encoded messages that are transmitted to it.

One important metric explored here is distance, which may be split into short-term, intermediate, and long-term history for each new concept depending on where and when it is encountered. Distance helps to determine which conceptual components to cluster as information regarding tendencies is being gathered. Based on patterns for each of these distance requirements, the author proposes a concept known as the "trigger pair," or a pair of word sequences whose probability of occurring within long-term history parameters is above some preset threshold. When the first phrase occurs, the second is triggered in predictive analysis, causing the probability function to change. Given a high enough probability p, each element in a trigger pair appears as follows:

$$W: \{W = w \text{ i.e. } W \text{ is the next word.}\} \tag{1}$$

$$W_o: \{W \in h, \text{ i.e. } W \text{ occured anywhere in the document history}\} \tag{2}$$

Mutual information may then be constructed between trigger pairs using a probability function, where A and B are:

$$I(A_o : B) = P(A_o, B)\frac{P(B/A_o)}{P(B)} + P(A_o, \overline{B})\frac{P(\overline{B}/A_o)}{P(\overline{B})} + P(\overline{A_o}, B)\frac{P(B/\overline{A_o})}{P(B)} + P(\overline{A_o}, \overline{B})\frac{P(\overline{B}/\overline{A_o})}{P(\bar{\bar{B}})} \tag{3}$$

The FCU uses a concept similar to the trigger pair in relating S+/R− events in neuronal interaction to the prime frequency oscillations that drive linguistic cognitive output. First, for each brain region identified in empirical studies, a set of concepts, brain regions and mappings may be defined between related concepts. Beginning with a set S (infinite) representing brain regions that may be activated by some means a number of additional steps may be taken to construct the concept set framework (with descriptions of symbols used in the concept set framework outlined in FIG. 2):

1) Introduce an σ-algebra. Next, a second set W is introduced whose elements are labeled concepts in the brain that correspond to words. For some subset A⊂A there is a mapping P: a∈A→w∈W, which may be termed the concept activation mapping. The elements a of A are action potentials.
2) Let P̃:w∈W→ã∈Ã be a mapping, which may be termed the brain activation mapping. Let μ be a measure on S and let F:A→{+,−} be a parity mapping. An axiology is a mapping Ξ:W→{+,−} generated by computing with and then projecting.

S is a set of sets of neurons classified according to neural topology as well as their tendency to activate in unison. Let λ be another weight mapping on some S∈S, such that λ assigns a greater probability of brain region activation of S to a subset of the neurons in S of size n. A Maxent mapping of S to W forms the initial layer of analysis, so that when W is later mapped to A, there is already a framework in existence for analyzing the brain regions and neuronal networks that become active when some concept w is introduced, either independently or in spoken dialogue. One of the primary uses is to address statistical anomalies, such as mis-speech, momentary confusion, or other events that may skew FCU analysis in an erroneous direction. In addition, Maxent can be used to reinforce recurring set and concept activations, such as in the recall of sensory phenomena, such as the taste or smell of a specific food.

Neurons do not statically integrate information in the way that transistors do. In addition, the electric fields generated by neuronal activity in turn can affect that very activity. Thus, since the binary mathematical principles that guide discrete transistor-based computation do not map particularly well to the brain, it is necessary to seek a more holistic view, hence the FCU. The Fundamental Code Unit (FCU) may unify multiple sensor data streams, such as linguistic input which is considered here, neurological data, such as cell and network activation, and neural firing rate and amplitude, and behavioral phenomena, such as nervous tics, spatial judgment errors, and gait irregularities, into a single computationally efficient framework. Because data collection methods will never achieve perfection, and due to the inherent uncertainty in physiologically complex processes such as cognition, there will always be some degree of missing or conflicting information in FCU classification and construction. To that end, maximum-entropy statistical models may be used to account for this uncertainty, as well as provide innovative Big Data predictive analytical-based capabilities for events that have yet to take place.

5. IMPLICATIONS OF A UNIT-BASED APPROACH.

5.1 Axiology of Human Thought: the Unitary System. The brain behaves in many different ways, its outputs manifested in physical movements and behaviors. Language, an expression of behavior is thus a useful tool in analyzing brain function. There is a transition from the molecular to the behavioral expressions of interactions of brain functions, such as the stochastic signaling phenomenon discussed above, which translates to language, and that a better understanding of axiology can disambiguate this process transition. The fundamental distinction within all languages, such as between semantic primes and non-primes or idiomatic words/expressions, is significant in that the cognitive processes leading to their acquisition are also distinct; thus, conceptual divides such as these, both in linguistics and psychology, provide important patterns to search out in the process of tying this concept of semantic primitives to the notion of stochastic signaling.

Axiology is a direct, multi-faceted description of a structure and function of the human language. It can aid in understanding perceptions, as well as in unifying the biochemical and cognitive structural aspects of conscious thought. The axiological model creates a code, the G code, which is unified and omnipresent within brain function. The G code defines the 'how' of each action in the outcome of the brain's decisions, as the code is being generated and executed on different media, but produces the same outcome: language. Thus, in order to dissect this code, it is useful to analyze language, which is based in axiology.

The central problem of axiology consists of issues in value and value theory. Values make up polar pairs; they are clear-cut dichotomies. They are either positive or negative, and the determination is made by intuition and inference. That which is intrinsically valuable is that which is inherently good, while that which is extrinsically valuable has value instrumental to something else. This example may be extended to include the creation of a mapping of axiological values to neurological state changes; in this way, two interdependent levels of cognitive analysis may be unified and provide a clearer picture of the components and structure of cognition.

Axiological semantics involves an examination of values with reference to the meaning of various linguistic expressions. The task of axiological semantics is to describe values and the manner in which they determine the structure and functioning of the human language as manifesting in communication. Preconceptual image schemata (which provide a format for encoding information from vision and language simultaneously) may include the axiological parameter PLUS-MINUS or positive-negative. For example, all such schemas, like values, exhibit a bipolar property of conferring positive or negative associations. All schemas may be understood to have euphoric or dysphonic characteristics. Axiological concepts emerge from axiological poles of preconceptual schemas through metaphorical extensions. Consequently, all words and linguistic symbolic units are assessable on an axiological scale. Even if words seem to be axiologically neutral, they are still prone to axiological distinction given appropriate contexts.

There is a formal scientific way to identify and rank human values, achieving values appreciation, values clarification, and values measurement since they are cognizable. The experience of value involves feeling, volition, desire, and an acquaintance with the object of value; this is a noetic feature. If considered coordinates of human actions—and when their finality is distinguished from their efficiency—qualitative values may become, within some limits, quantifiable. However, the primary relational determinant of value is polarity. Thus, an axiological parameter may be defined.

In some models, the concept of a value may be explicable only in terms of good, bad, and indifferent. For example, an individual with a "positive" state of mind may be happy and content, while an individual with a "negative" state of mind may be sad and unsatisfied. This interpretation undermines the idea that the use of language extends beyond its semantic features and functions and overlooks the principle that there may be various apparatuses for construal. Therefore, the positive-negative evaluation cannot be limited to the good-bad and the happy-sad scale, for it is only one dimension of the axiological parameter. Thus, time orientation schema may also be considered. For example, "positive" may be analogous to "future-oriented" and "negative" may be analogous to "past-oriented."

Human beings, are uniquely motivated to orient themselves in relation to time. It is the sense of future-ness that enables maturation beyond a psychopathic stage. The parallel nature of memory and future thinking may be considered as processes involving reliving the past and pre-living the future. For example, an individual's actions, emotions, and morale may depend on his or her aspirations in relation to time perspective. The motivational power of constructed future images and their development across age may also be important. An individual's attitude toward time might be as significant as personality traits like optimism or sociability when assessing mental stat. Time perspective influences judgments, decisions, and actions. Since linguistic expression corresponds to mental state, the logical assumption that words reflect time perspective may be adopted.

To develop a "default axiology"; first the "intrinsic value" of words that have been characterized as semantic primes may be determined based on the positive-negative axiological parameter. A semantic prime is a linguistic expression whose meaning cannot be presented in any simpler terms. It has a lexical equivalent in all languages. In cases where the intrinsic value of a word is ambiguous it is useful to consider the antonym of the word to determine its value. To determine the axiological value of linking and auxiliary verbs, the "temporal value" of words based on the past-future scale may be considered. While intrinsic value of these verbs may be ambiguous, a positive or negative grammatical axiological value may still be assigned to these words. Verbs in the future tense indicate future-oriented perspective and should be designed as positive. Verbs in the past tense indicate past-oriented perspective and should be noted as negative.

The "consequent value" of words for which the intrinsic value is not immediately apparent may also be determined. For example, closed class words, or those that are less definable in terms of other words, have less readily identifiable meaning and thus, it is difficult to assign an axiological value to these words. However, the value of surrounding words in the passage provides context that can be used to determine value. Consequently, the cognitive model suggests that a grammatical subsystem can also be semantically characterized. This view entails a continuum between openand closed-class within the knowledge base. Thus, the value of closed-class words can be determined by their context within a phrase or sentence.

However, when people speak, they combine words into sentences. Thus, it becomes necessary to determine the positive or negative value of an expression and derive aggregate values. The linguistic constructs that describe values may present as manifestations of the brain structures that are involved in generating and analyzing discourse and ultimately behavior. Linguistic models, such as Language Axiological Input/Output system (LXIO), a mood analyzer system for discourse, enable us to determine the values of expression in language, thus providing insight into brain structure and function.

5.2 Molecular Chirality and Cognition. One can see the unitary system functioning at the molecular level in the molecular chirality concept. At a synapse, a neuron releases neurotransmitters that excite or inhibit another cell or alter its response to other input. Excitatory neurotransmitters, the most common type, increase the firing rate. An inhibitory neurotransmitter decreases the chances of the neuron firing. This is the most common type, while still others increase firing rate (or the chances that the next neuron will fire). Each neuron is influenced via multiple neurotransmitters acting at multiple synapses by dozens of other neurons. Assuming that neurotransmitters are composed of the 22 proteins, are used in biology (and the number may be smaller), and let L be the average number of proteins in a neurotransmitter, then the entropy of the neurotransmitter space is 22L. The relationship of neurotransmitter geometries to one another and to geometry of neuroreceptors gives rise to complex absorption behavior. A tight match can lead to reliable high rates of uptake, while less perfect matches can lead to lower and/or more stochastic uptake behavior. The use of particular sequences of wave of transmitters can condition rates of uptake.

Following the release of a neurotransmitter and the subsequent activation of a receptor, it is important that the response is terminated and the system reset so that a subsequent activation can occur. This is achieved via the removal of the neurotransmitter by metabolic enzyme activity and by passive or active uptake activities. The concentration of the transmitter at the synapse for a longer time period occurs if the uptake mechanism is blocked. Therefore, a neurotransmitter uptake blocker may have an effect similar to a postsynaptic agonist of that transmitter. For uptake to take place, the neurotransmitter must be recognized by an uptake mechanism. As a result, it is common for structural analogs of the neurotransmitter of this process, for example, noradrenaline, serotonin, and dopamine. Once again, the unitary system is at work in the form of chirality, as explained below.

Biological molecules, such as neurotransmitters, exist in mirror image isomers of one another, and this is what governs the ligand-substrate interaction specificity necessary for biochemical reactions. The recognition of a neurotransmitter by its complementary receptor occurs due to the unique conformation of each isomer-enantiomer ligand, functioning in a lock and key mechanism. The two-mirror image isomer-enantiomer molecules will interact with postsynaptic receptors, producing different biochemical effects. The ligand-substrate specificity required for neurotransmitter activity is conferred by the unique electronic interactions between asymmetric molecules. The all-or-nothing action potential is generated by the summation of excitatory and inhibitory signals in the form of chiral molecules that are found in a S(+) or R(−) isomer-enantiomer conformation binding and releasing from the receptor, generating a strong enough signal to cause the neuron to reach threshold. While the chiral neurotransmitters are mirror images of one another, it is important to remember that they are not the same molecule and will not exert the same strength of signal upon the receptor. The salience of the signal is determined by the strength of the ligand-substrate interaction.

While it may not be the case with regard to all stimulant actions, particularly those produced in the periphery, such as cardiovascular actions, with respect to the central stimulant actions on a regional structure of the central nervous system, the S(+) isomer is several times more potent than its R(−) enantiomer. The S(+) isomer is known to induce euphoria, whereas enantiomer R(−) causes depression. The overall greater potency of the S(+) isomer form with respect to central stimulant actions suggests that this form may have a higher potential for deep cranial stimulant actions and neurotransmitters availability in the synapse. This leads to behavioral-alteration notice on corresponding linguistics states. The correlations of the LXIO system and S(+) isomer and R(−) enantiomer values offer corresponding equivalence of transporter's chemical pathways. Thus, mood states are viewed at the molecular and behavioral level, whereas prior research only proposed framework for neuronal correlation based on constellations activity in imagery. Addition of R(−) enantiomer into pharmaceutical treatment provides them with a quicker onset and longer clinical effect compared to pharmaceuticals exclusively formulated using the S(+) isomer. Nevertheless, it seems the human brain favors S(+) isomer over R(−) enantiomer. Central stimulants exert their effects by binding to the monoamine transporters and increasing extracellular levels of the biogenic amines dopamine, norepinephrine, and serotonin.

The S(+) isomer acts primarily on the dopaminergic (DA) systems, while R(−) enantiomer acts primarily on norepinephrinergic (NE) systems. Consequently, the primary reinforcing and behavioral-stimulant effects of the S(+) isomer are linked to enhanced dopaminergic activity, primarily in the mesolimbic dopaminergic pathway. S(+) isomers bind to the dopamine transporter (DAT) and blocks the transporter's ability to clear DA from the synaptic space. In addition, the S(+) isomer is transported into the cell, which leads to dopamine efflux (DA is transported out of the cell and into the synaptic space via reverse transport of the DAT). In high doses, the S(+) isomer and R(−) enantiomer can also inhibit the enzymes monoamine oxidase A and B (MAO-A and MAO-B). MAO-A is responsible for breaking down serotonin, dopamine, norepinephrine, and epinephrine. MAO-B is responsible for breaking down dopamine (more potently than MAO-A) and phenylethylamine (PEA), which has actions similar to the S(+) isomer itself, and is thought to be involved in feelings of lust, confidence, obsession, and sexuality. The ability of S(+) isomer, and to a lesser extent R(−) enantiomer, to inhibit MAO-A and MAO-B, results in the accumulation of monoamines. Thus, central stimulant actions directly excite the release of these neurochemicals, which results in a potent elevation in monoamine neurotransmission. In sum, the effect of a central stimulant, the S(+) isomer and to lesser extent R(−)enantiomer, is to increase neurotransmitter availability in the synapse, by both releasing more neurotransmitters, as well as prolonging their availability in the synapse by slowing their removal.

The S(+) isomer and R(−) enantiomers are the most important part of the chemical exchange at the molecular level of neurobiological information exchanges. These forms may explain the structure that is present in the fundamental code unit, and illuminate which parts of stochastic signaling, for example, energy spikes or spike intervals, most closely correlate with conscious cognitive expression. Ultimately, these molecules that govern molecular informational exchanges are the physical mechanisms by which the Unitary System manifests itself in the human brain; using unary mathematics we create a model by which the chemical and physical aspects of cognition are converted into a coding of human thought that is both computationally meaningful and understandable to humans.

6. Genetic vs. Cognitive Information Storage: Links and applications. Human cognition is an inherently physical process. Given enough time and sufficiently sensitive instruments, human thoughts could be reduced to patterns of electrochemical as well as atomic and subatomic phenomena. However, cognition is much more complex than the sum of its parts. To rely upon instrumentation alone in the quantification of cognitive phenomena would be to misunderstand the sheer complexity of the brain's internal structure and function. The brain's structure is derived from genetics, but genetics do encode the layers of complexity added by experiences, sensations, and new connections. These neural networks are densely interconnected which are thought to play vital roles in cognitive functions and information integration. To that end, our research is a codification of the most basic unit of cogent thought, from which conscious thoughts can be assembled.

7. Summary. The Fundamental Code Unit of Thought (FCU) is an attempt to bridge this gap between the physical phenomena we observe and their complex results. The FCU consists of two essential components. The framework itself can also be considered a trans-disciplinary informational container that spans a number of analytical and physical dimensions. Due to the fact that cognition is both a physical and computational (i.e. conceptual) occurrence, any benchmark by which we hope to measure it must take both of these into account. The underlying units that compose cognition, like those of DNA, are relatively simple compared with the structures they create. This applies both to the brain itself and the way we perceive it (i.e., as a system of sensory inputs and linguistic and behavioral outputs). In our approach, we map the physical phenomena of cognition to this theoretical system.

In addition to the FCU, a conception of brain language may include the mathematical framework in which the FCU is located. The Unitary System is founded on unary mathematics. The functions "unary plus" (+) and "unary minus" (−), representing an increase or decrease in the underlying measured value, carry sufficient computational efficiency to represent human cognition, provided that the same linguistic base is present on both sides. The brain communicates within itself and with the rest of the body via unitary operators. These unitary operators carry a state of time and space that conveys information necessary to decipher any semantic or non-semantic based language. Because these operators are language-agnostic, they provide a common language of cognition when the FCU is applied.

DNA and its cognitive equivalent, the Unitary System/FCU, are not only conceptually linked but physically linked as well. In a recent paper published by the Proceedings of the National Academy of Sciences, this concept is examined in more detail, in a "rewriteable recombinase addressable data (RAD) module that reliably stores digital information within a chromosome." How is genetic information storage tied to cognitive information storage? Each has a distinct biological foundation (the latter is driven by recombinase proteins), so the dimensionality of the information is similar, as is the stochasticity: "stochasticity in RAD system performance arising from bidirectional recombination can be achieved and tuned by varying the synthesis and degradation rates of recombinase proteins."

8. Conclusion. The ability to use existing biological structures such as proteins and chromosomes to store information means that biological bit-encoding is increasingly feasible, despite the fact that the brain has been performing this process for eons.

Using unary mathematics, and unifying external data with internal processes, can help achieve the outcome of pertinent thoughts in opposite situations—the most complex decision-making process performed by the brain.

Figure 4:
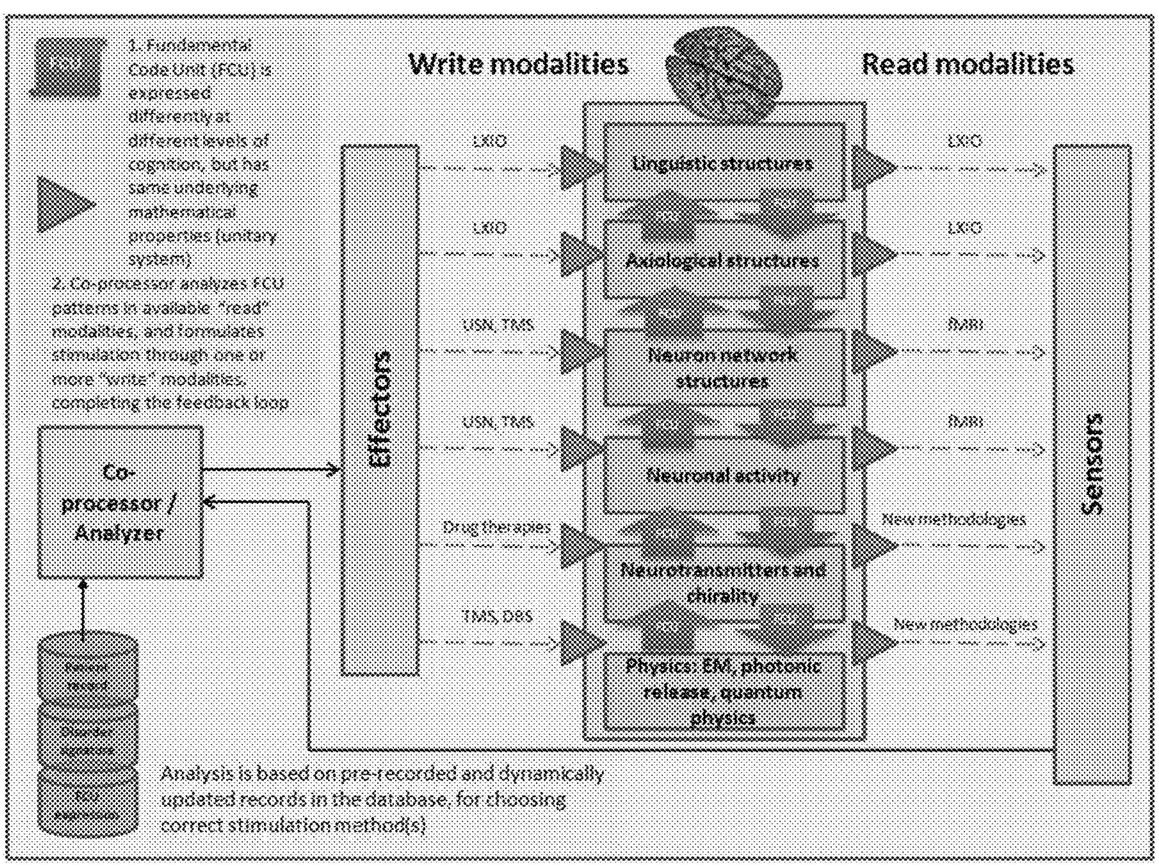
FIG. 4 is an exemplary illustration of multi-level neurofeedback using FCU analysis.

An example of multi-level neurofeedback using FCU analysis is shown in FIG. 4. FIG. 4 provides a higher-level view of the relationship between sensors, or read modality elements, and effectors, or write modality elements. Each of these exists in a cyclic relationship with the next. The dual process of querying by read modalities and application of write modalities varied by type, duration and intensity is computed by unary mathematics of FCU and is used to diagnose and treat complex neurological disorders.

Figure 5:
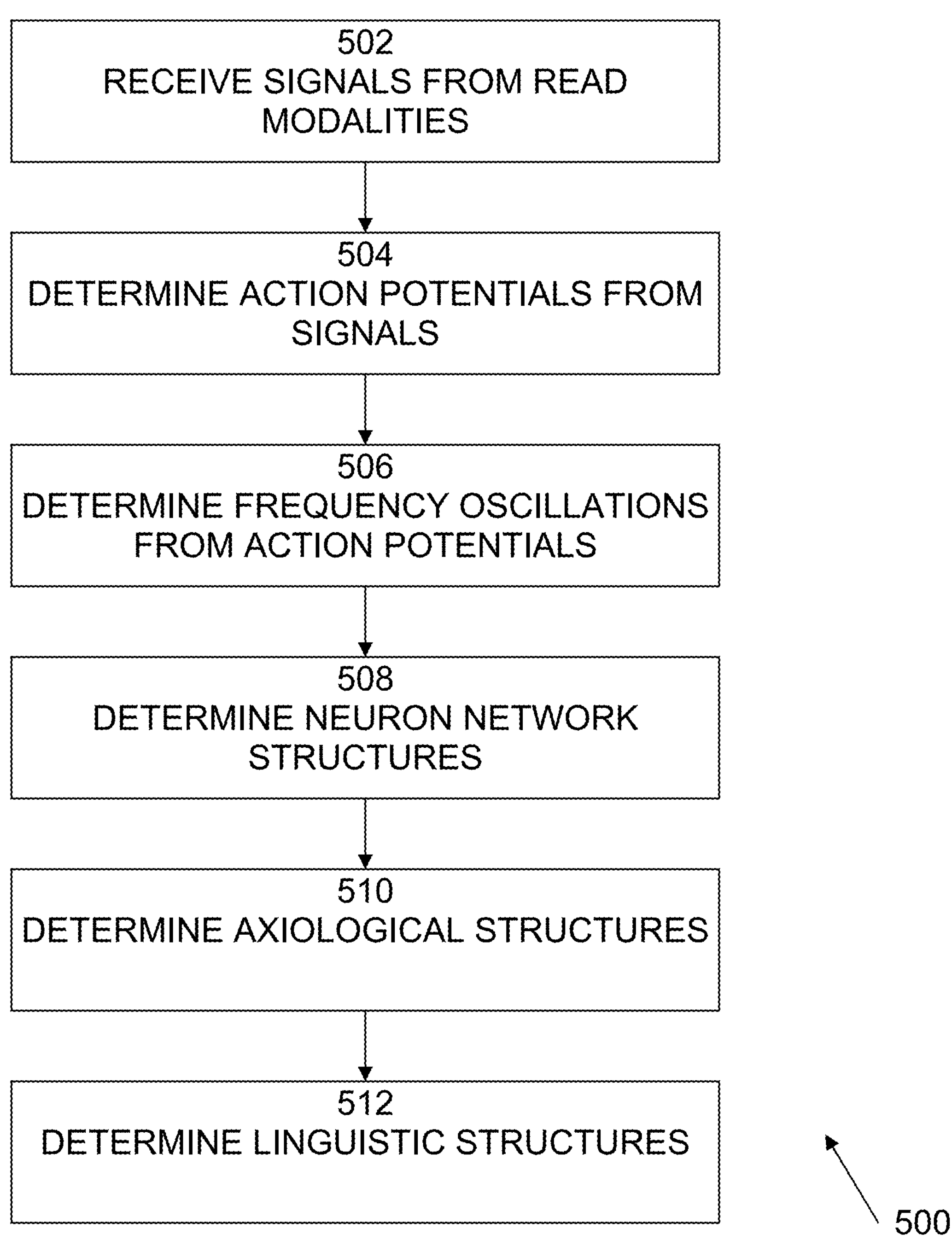
FIG. 5 is an exemplary flow diagram of a process of translation from neuronal interaction to cognition and language.

An exemplary flow diagram of a process 500 of translation from neuronal interaction to cognition and language is shown in FIG. 5. Process 500 begins with 502, in which signals representing physical conditions and activity of neural tissue may be received from read modalities. For example, such signals may be electrical or optical, and may correspond to neurotransmitter and spike/pulse sequences, etc. At 504, action potentials may be determined based on the signals received from the read modalities. At 506, frequency oscillations may be determined based on the signals received from the read modalities and the action potentials. At 508, neuron network structures may be determined based on the signals received from the read modalities, the action potentials, and the frequency oscillations. For example, this process may use a concept similar to the trigger pair in relating S+/R− events in neuronal interaction to the prime frequency oscillations that drive linguistic cognitive output, as described above. At 510, axiological structures may be determined based on the signals received from the read modalities, the action potentials, the frequency oscillations, and the determined neuron network structures. Axiology is a direct, multi-faceted description of a structure and function of the human language, as described above. At 512, linguistic structures may be determined based on the signals received from the read modalities, the action potentials, the frequency oscillations, the determined neuron network structures, and the determined axiological structures.

Figure 6:
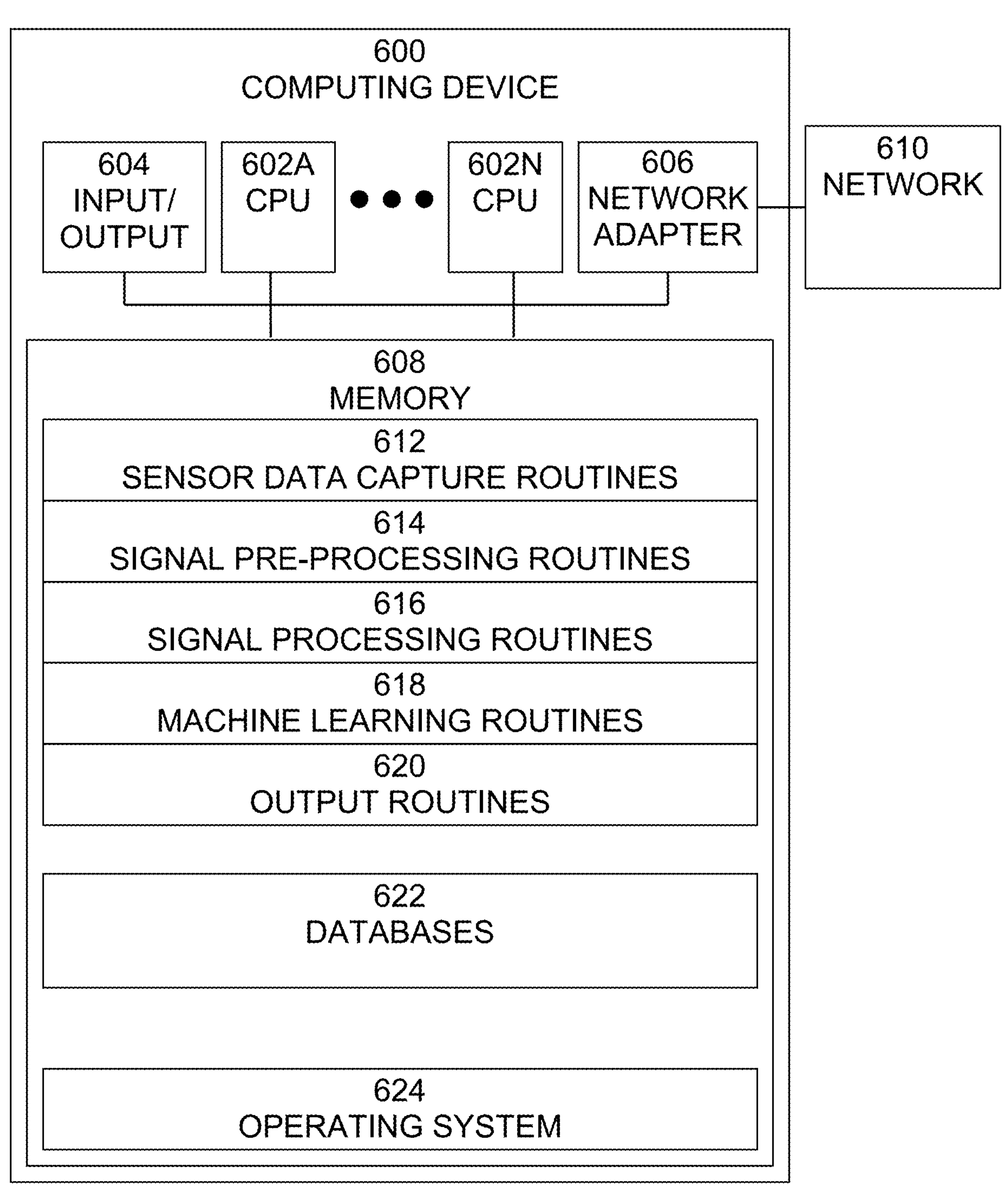
FIG. 6 is an exemplary block diagram of a computing device in which processes involved in the embodiments described herein may be implemented.

An exemplary block diagram of a computing device 600, in which processes involved in the embodiments described herein may be implemented, is shown in FIG. 6. Computing device 600 may be a programmed general-purpose computer system, such as an embedded processor, microcontroller, system on a chip, microprocessor, smartphone, tablet, or other mobile computing device, personal computer, workstation, server system, and minicomputer or mainframe computer. Computing device 600 may include one or more processors (CPUs) 602A-602N, input/output circuitry 604, network adapter 606, and memory 608. CPUs 602A-602N execute program instructions in order to carry out the functions of the present invention. Typically, CPUs 602A-602N are one or more microprocessors, such as an INTEL PENTIUM® processor. FIG. 6 illustrates an embodiment in which computing device 600 is implemented as a single multi-processor computer system, in which multiple processors 602A-602N share system resources, such as memory 608, input/output circuitry 604, and network adapter 606. However, the present invention also contemplates embodiments in which computing device 600 is implemented as a plurality of networked computer systems, which may be single-processor computer systems, multi-processor computer systems, or a mix thereof.

Input/output circuitry 604 provides the capability to input data to, or output data from, computing device 600. For example, input/output circuitry may include input devices, such as keyboards, mice, touchpads, trackballs, scanners, etc., output devices, such as video adapters, monitors, printers, etc., and input/output devices, such as, modems, etc. Network adapter 606 interfaces device 600 with a network 610. Network 610 may be any public or proprietary LAN or WAN, including, but not limited to the Internet.

Memory 608 stores program instructions that are executed by, and data that are used and processed by, CPU 602 to perform the functions of computing device 600. Memory 608 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 608 may vary depending upon the function that computing device 600 is programmed to perform. For example, as shown in FIG. 1, computing devices may perform a variety of roles in the system, method, and computer program product described herein. For example, computing devices may perform one or more roles as end devices, gateways/base stations, application provider servers, and network servers. In the example shown in FIG. 6, exemplary memory contents are shown representing routines and data for all of these roles. However, one of skill in the art would recognize that these routines, along with the memory contents related to those routines, may not typically be included on one system or device, but rather are typically distributed among a plurality of systems or devices, based on well-known engineering considerations. The present invention contemplates any and all such arrangements.

In the example shown in FIG. 6, memory 608 may include sensor data capture routines 612, signal pre-processing routines 614, signal processing routines 616, machine learning routines 618, output routines 620, databases 622, and operating system 624. For example, sensor data capture routines 612 may include routines that interact with one or more sensors, such as EEG sensors, and acquire data from the sensors for processing. Signal pre-processing routines 614 may include routines to pre-process the received signal data, such as by performing band-pass filtering, artifact removal, finding common spatial patterns, segmentation, etc. Signal processing routines 616 may include routines to process the pre-processed signal data, such as by performing time domain processing, such as spindle threshold processing, frequency domain processing, such as power spectrum processing, and time-frequency domain processing, such as wavelet analysis, etc. Machine learning routines 618 may include routines to perform machine learning processing on the processed signal data. Output routines 620 may include software routines to generate stimulus commands to provide stimulus waveforms so as to perform Fundamental Code Unit Unary signaling as described above. Databases 622 may include databases that may be used by the processing routines. Operating system 624 provides overall system functionality.

As shown in FIG. 6, the present invention contemplates implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry (such as that shown at 208 of FIG. 2) may include, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims. Further, it is to be noted that, as used in the claims, the term coupled may refer to electrical or optical connection and may include both direct connection between two or more devices and indirect connection of two or more devices through one or more intermediate devices.

What is claimed is:

1. A computer-implemented method executable by a processor including a memory for determining structure of living neural tissue comprising:

receiving at least one photonic signal from at least one read modality, the at least one photonic signal representing at least one physical condition of the living neural tissue;

determining an action potential based on the at least one photonic signal received from the at least one read modality;

determining a frequency oscillation based on the at least one photonic signal received from the at least one read modality and the action potential;

determining neuron network structures that indicate observable linguistic events based on the photonic signals received from the read modalities, the action potentials, and the frequency oscillations, wherein the neuron network structures are determined using a Maximum Entropy model; and stimulating the living neural tissue utilizing at least one write modality based on the neuron network structures and the at least one read modality.

2. The method of claim 1, further comprising determining axiological structures based on the photonic signals received from the read modalities, the action potentials, the frequency oscillations, and the determined neuron network structures.

3. The method of claim 2, wherein the axiological structures are determined using a Unitary System in which preconceptual image schemata include axiological parameters with bipolar properties having positive and negative associations.

4. The method of claim 3, further comprising determining linguistic structures based on the photonic signals received from the read modalities, the action potentials, the frequency oscillations, the determined neuron network structures, and the determined axiological structures.

5. The method of claim 4, wherein the linguistic structures are determined by assessing linguistic symbolic units on an axiological scale.

6. A system for determining structure of living neural tissue, the system comprising a processor, memory accessible by the processor, and computer program instructions stored in the memory and executable by the processor to perform:

receiving at least one photonic signal from at least one read modality, the photonic signal representing at least one physical condition of the living neural tissue;

determining an action potential based on the at least one photonic signal received from the at least one read modality;

determining a frequency oscillation based on the at least one photonic signal received from the at least one read modality and the action potential;

determining neuron network structures that indicate observable linguistic events based on the photonic signals received from the read modalities, the action potentials, and the frequency oscillations, wherein the neuron network structures are determined using a Maximum Entropy model;

stimulating the living neural tissue utilizing at least one write modality based on the neuron network structures and the at least one read modality.

7. The system of claim 6, further comprising determining axiological structures based on the photonic signals received from the read modalities, the action potentials, the frequency oscillations, and the determined neuron network structures.

8. The system of claim 7, wherein the axiological structures are determined using a Unitary System in which preconceptual image schemata include axiological parameters with bipolar properties having positive and negative associations.

9. The system of claim 8, further comprising determining linguistic structures based on the photonic signals received from the read modalities, the action potentials, the frequency oscillations, the determined neuron network structures, and the determined axiological structures.

10. The system of claim 9, wherein the linguistic structures are determined by assessing linguistic symbolic units on an axiological scale.

11. A non-transitory computer program product for determining structure of living neural tissue, the computer program product comprising a non-transitory computer readable storage having program instructions embodied therewith, the program instructions executable by a computer including a processor and memory, to cause the computer to perform a method comprising:

receiving at least one photonic signal from at least one read modality, the photonic signal representing at least one physical condition of the living neural tissue;

determining an action potential based on the at least one photonic signal received from the at least one read modality;

determining a frequency oscillation based on the at least one photonic signal received from the at least one read modality and the action potential;

determining neuron network structures that indicate observable linguistic events based on the photonic signals received from the read modalities, the action potentials, and the frequency oscillations, wherein the neuron network structures are determined using a Maximum Entropy model;

stimulating the living neural tissue utilizing at least one write modality based on the neuron network structures and the at least one read modality.

12. The computer program product of claim 11, further comprising determining axiological structures based on the photonic signals received from the read modalities, the action potentials, the frequency oscillations, and the determined neuron network structures.

13. The computer program product of claim 12, wherein the axiological structures are determined using a Unitary System in which preconceptual image schemata include axiological parameters with bipolar properties having positive and negative associations.

14. The computer program product of claim 13, further comprising determining linguistic structures based on the photonic signals received from the read modalities, the action potentials, the frequency oscillations, the determined neuron network structures, and the determined axiological structures.

15. The computer program product of claim 14, wherein the linguistic structures are determined by assessing linguistic symbolic units on an axiological scale.

* * * * *